US010682206B2

(12) United States Patent
Gottenbos et al.

(10) Patent No.: US 10,682,206 B2
(45) Date of Patent: Jun. 16, 2020

(54) NOZZLE FOR POWDER DELIVERY WITH A PERSONAL CARE APPLIANCE AND METHOD

(71) Applicant: KONINKLIJKE PHILIPS N.V., Eindhoven (NL)

(72) Inventors: Bart Gottenbos, Budel (NL); Lieven Adriaenssen, Vilvoorde (BE); Helle Ullerup, Mol (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1 day.

(21) Appl. No.: 15/564,208

(22) PCT Filed: Apr. 4, 2016

(86) PCT No.: PCT/IB2016/051901
§ 371 (c)(1),
(2) Date: Oct. 4, 2017

(87) PCT Pub. No.: WO2016/162782
PCT Pub. Date: Oct. 13, 2016

(65) Prior Publication Data
US 2018/0125608 A1 May 10, 2018

Related U.S. Application Data

(60) Provisional application No. 62/143,329, filed on Apr. 6, 2015.

(51) Int. Cl.
*A61C 3/025* (2006.01)
*A61C 1/08* (2006.01)
(Continued)

(52) U.S. Cl.
CPC ............ *A61C 3/025* (2013.01); *A61C 1/0061* (2013.01); *A61C 1/08* (2013.01); *A61C 1/087* (2013.01);
(Continued)

(58) Field of Classification Search
CPC ........... A61C 3/025; A61C 1/087; A61C 1/08; A61C 1/08061; A61C 1/0061;
(Continued)

(56) References Cited

U.S. PATENT DOCUMENTS

| 4,540,365 A | * | 9/1985 | Nelson | A61C 3/025 433/125 |
| 5,857,851 A | | 1/1999 | Chavanne | |
| 6,093,021 A | * | 7/2000 | Rainey | A61C 3/025 433/88 |
| 6,164,967 A | * | 12/2000 | Sale | A46B 11/002 15/22.1 |

(Continued)

FOREIGN PATENT DOCUMENTS

| EP | 2774575 A2 * | 9/2014 | ............ A61C 3/025 |
| WO | 2013093816 A1 | 6/2013 | |

(Continued)

*Primary Examiner* — Sean M Michalski
*Assistant Examiner* — Shannel N Wright

(57) ABSTRACT

A powder delivery nozzle (12) for a personal care appliance (10) comprises a body (28), guidance tip (38), powder chamber (50), and flexible membrane (56). The body (28) includes an air-liquid channel (30) for delivery of air and/or liquid from a proximal end to a distal end thereof. The guidance tip (38), located at the distal end of the body (28), includes an orifice (40) coupled to the air-liquid channel (30) and is configured to expel a pulse of air and/or liquid. The powder chamber (50) is configured for storing a powder (52) and having an air intake port (42) and a powder outlet port (44). The flexible membrane (56) is disposed between the powder chamber (50) and the air-liquid channel (30). Responsive to delivery of a pulse of air and/or liquid via the air-liquid channel (30), a pulse of pressure is applied to the flexible membrane (56) for actuating a release of powder
(Continued)

expelled from the powder chamber (50) via the powder outlet port (44). A method and personal care appliance are also disclosed.

14 Claims, 4 Drawing Sheets

(51) Int. Cl.
 *A61C 1/00* (2006.01)
 *A61C 17/02* (2006.01)
 *A61K 8/02* (2006.01)

(52) U.S. Cl.
 CPC ........ *A61C 17/0202* (2013.01); *A61K 8/0241* (2013.01)

(58) Field of Classification Search
 CPC . A61C 17/0202; A61C 17/022; A61C 17/028; B24C 7/0069; B24C 7/0089; B24C 7/0084
 USPC .................................................. 433/86–89, 96
 See application file for complete search history.

(56) References Cited

U.S. PATENT DOCUMENTS

| 8,591,231 | B1* | 11/2013 | Wolske | ................ | A61C 17/005 |
|---|---|---|---|---|---|
| | | | | | 433/125 |
| 8,672,678 | B2 | 3/2014 | Gramann et al. | | |
| 2004/0202980 | A1* | 10/2004 | Policicchio | ............ | A61C 3/025 |
| | | | | | 433/88 |
| 2005/0202364 | A1* | 9/2005 | Fornasari | ............... | A61C 3/025 |
| | | | | | 433/88 |
| 2005/0233280 | A1 | 10/2005 | Hamman | | |
| 2011/0066132 | A1* | 3/2011 | Ji | ........................ | A61M 13/00 |
| | | | | | 604/500 |
| 2011/0178495 | A1* | 7/2011 | Ji | ........................ | A61M 13/00 |
| | | | | | 604/500 |
| 2015/0017601 | A1* | 1/2015 | Fish | ...................... | A61C 3/025 |
| | | | | | 433/88 |
| 2016/0015479 | A1 | 1/2016 | Yamane et al. | | |
| 2018/0193108 | A1* | 7/2018 | Guenst | ................ | A61C 1/0092 |

FOREIGN PATENT DOCUMENTS

WO 2014099800 A1 6/2014
WO 2014136846 9/2014

\* cited by examiner

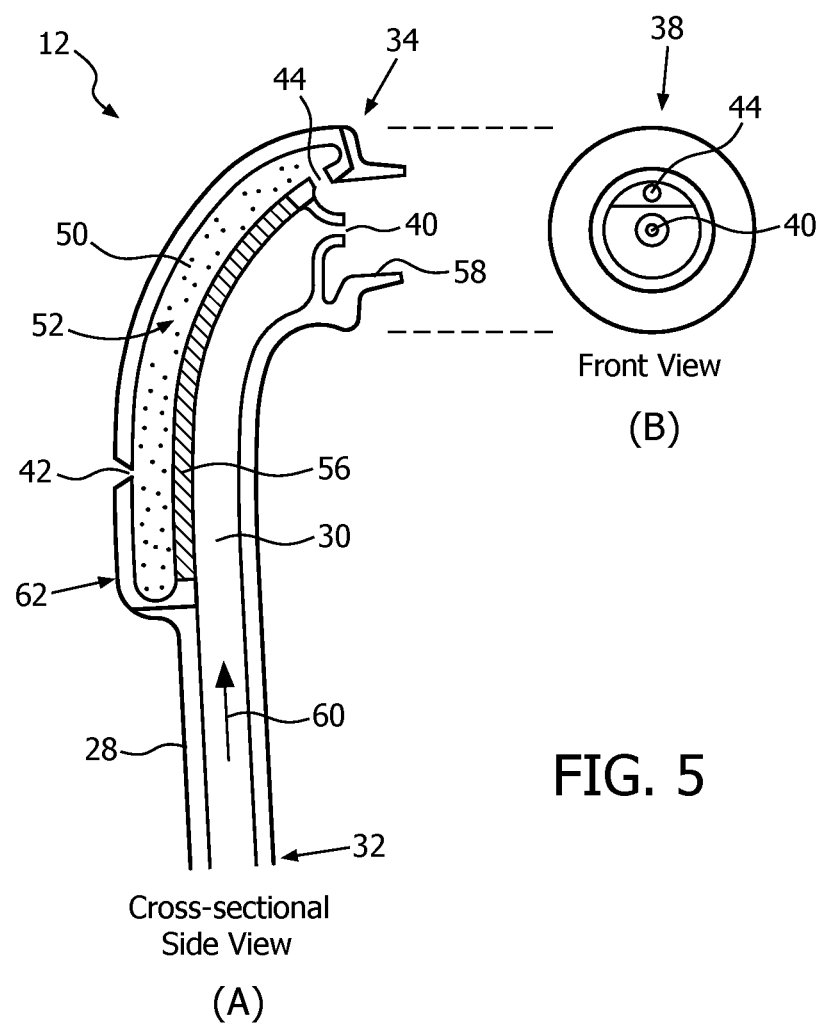

_US 10,682,206 B2_

NOZZLE FOR POWDER DELIVERY WITH A PERSONAL CARE APPLIANCE AND METHOD

CROSS-REFERENCE TO PRIOR APPLICATIONS

This application is the U.S. National Phase application under 35 U.S.C. § 371 of International Application No. PCT/IB2016/051901, filed on Apr. 4, 2016, which claims the benefit of U.S. Provisional Patent Application No. 62/143,329, filed on Apr. 6, 2015. These applications are hereby incorporated by reference herein.

The present embodiments relate generally to personal care appliances and more particularly, to a nozzle for powder delivery with a personal care appliance and a method.

For smart sustained release of oral therapeutic agents for oral care, using dry particles offers a number of advantages over the use of particle suspensions in liquid. Some agents can for example not be easily formulated in a stable liquid formulation, while they can have a long shelf life when formulated in a dry particle. Examples of such agents are hydrogen peroxide combined with its activators; enzymes; probiotics, etc. Further when delivering particles from suspension, the particle properties need to be tuned for fast adhesion to the teeth or other oral surfaces. For dry particles this is less the case since these will immediately adhere to the saliva film present on the teeth due to capillary forces.

It can be appreciated that the Philips Sonicare™ AirFloss™ technology, generating an air pulse in the device with a cylinder, can be a usable drive train to propel dry particles towards the teeth with the air flow created. The AirFloss™ platform seems to be particularly suitable for delivering dry particulate matter, compared to other oral care consumer devices.

Dry particles would need to be fed into the air stream to be transported towards the teeth. However, if this is done inside the AirFloss™ device, the dry particles will attach to the insides of the nozzle, clogging the nozzle and could also disadvantageously hamper delivery.

Accordingly, an improved method and apparatus for overcoming the problems in the art is desired.

In accordance with one aspect, a powder delivery nozzle for a personal care appliance comprises a body having at least one air-liquid channel configured for delivery of air, liquid, or a combination of air and liquid from a proximal end to a distal end thereof. A guidance tip is located at the distal end of the body, wherein the guidance tip includes an orifice coupled to the air-liquid channel and is configured to expel a pulse of air, liquid, or a combination of air and liquid. A powder chamber is provided for storing a powder and having at least one air intake port and at least one powder outlet port. A flexible membrane is disposed between a portion of the powder chamber and the air-liquid channel, wherein responsive to delivery of a pulse of air, liquid, or a combination of air and liquid via the air-liquid channel, a pulse of pressure is applied to the flexible membrane for actuating a release of powder expelled from the powder chamber via the powder outlet port. Advantageously, the powder is released outside the nozzle in the stream of air/liquid as it is being expelled from the nozzle.

In accordance with another aspect, the air intake port is configured for enabling air or an ambient gas to enter the powder chamber immediately subsequent to the release of powder expelled via the outlet port in proportion to a dose of powder expelled. In another embodiment, immediately subsequent to the release of powder, air or an ambient gas enters the powder chamber via the air intake port in proportion to an amount of powder expelled, in preparation for a subsequent delivery of powder. In one embodiment, the at least one air intake port comprises a one-way air intake valve and the at least one powder outlet port comprises a one-way ejection valve.

In accordance with another aspect, the powder outlet port is disposed within the guidance tip, proximate the orifice. In another embodiment, the powder outlet port is positioned within the guidance tip at a depth that comprises one selected from the group consisting of (i) at a same depth as that of the orifice and (ii) at a depth greater than a depth of the orifice within the guidance tip.

According to another aspect, the powder chamber further comprises at least one selected from the group consisting of (i) a chamber integrated within the body, and (ii) an exchangeable chamber configured for attachment to the body. In one embodiment, the powder chamber comprises the exchangeable chamber configured for attachment to the body, and the flexible membrane comprises a portion of the powder chamber. In another embodiment, the powder chamber comprises the exchangeable chamber configured for attachment to the body, and the flexible membrane comprises a portion of the nozzle body.

In accordance with a further aspect, the powder chamber comprises a refillable chamber having a refill aperture, wherein the refill aperture is configured (i) for being opened to enable refilling of the refillable chamber with powder and (ii) for being closed subsequent to refilling the refillable chamber with powder. In addition, the refill aperture includes a refill cap, wherein removal of the refill cap enables the refilling via the refill aperture and replacement of the refill cap facilitates closing of the refill aperture.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

Figure 4:
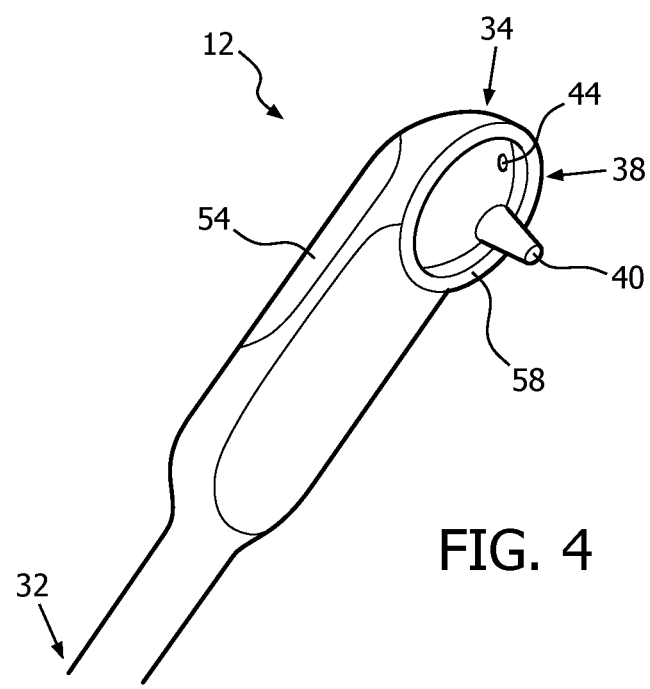

FIG. 4 is another perspective view of a powder delivery nozzle for use with the device for powder delivery to interproximal areas of teeth and for implementing a powder delivery procedure according to an embodiment of the present disclosure; and FIG. 5 is a schematic cross-sectional view of various components of a powder delivery nozzle for use with the device for powder delivery to interproximal areas of teeth and for implementing a powder delivery procedure according to another embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

Interproximal spaces generally refer to those areas in the mouth that are most prone to oral disease, since bacteria can easily accumulate in these hard-to-access sites. Common diseases like gingivitis and cavities are most prevalent in the interproximal space. Smart sustained release of oral therapeutic agents for oral care using dry particles delivered within and around the interproximal space may be able to prevent such diseases. As the areas of interproximal space are secluded, smart sustained release systems could be easily retained in the interproximal spaces, while on the alternative tooth surfaces (e.g. buccal/labial and lingual/palatal surfaces) such systems may be easily removed by, for example, eating.

In conjunction with the embodiments of the present disclosure, the inventors have found that dry powder formulations are ideal for smart/slow release of agents in the oral cavity, since the dry powder formulations have a long shelf life, can be delivered in the oral cavity using air-liquid flow, and stick immediately to wet oral surfaces (e.g. teeth), releasing the agents where they are needed. The current Philips Sonicare™ AirFloss™ technology can be used to drive the delivery of the powders, however, building a powder chamber in the handle is difficult and there is a high risk that the powder sticks to the wet insides of the nozzle, not effectively delivering the dry particles. According to the embodiments of the present disclosure, a specialized nozzle with powder chamber is disclosed, where powder release is driven by an air pulse, and the powder outlet is at the exit of the nozzle, to provide an optimal powder delivery. The powder chamber is attached to or integrated in the nozzle, and equipped with a flexible membrane towards the inside of the AirFloss™ air-liquid channel of the nozzle. The air pulse of the device delivers enough pressure to push, with each air-liquid shot, a dose of powder out of the powder chamber outlet into the stream of air-liquid outside the tip of the nozzle, directed towards the teeth. Different embodiments are disclosed herein, for example one with exchangeable powder chamber cartridges and one with a refilling device to refill the powder chamber.

As disclosed herein, in one embodiment, a design is proposed where only the nozzle is changed to achieve dry particle delivery. A powder chamber is integrated in the nozzle, with the powder exit at or close to the air-liquid exit of the nozzle. The chamber wall connected to the inside of the air-liquid channel is made of flexible material. When an air-liquid pressure pulse moves through the nozzle, the elevated pressure compresses the powder chamber, via the flexible material, releasing a dose of powder from the powder exit which ejects the powder in the airliquid stream transporting it to the teeth. Additional embodiments are also disclosed.

Figure 1:
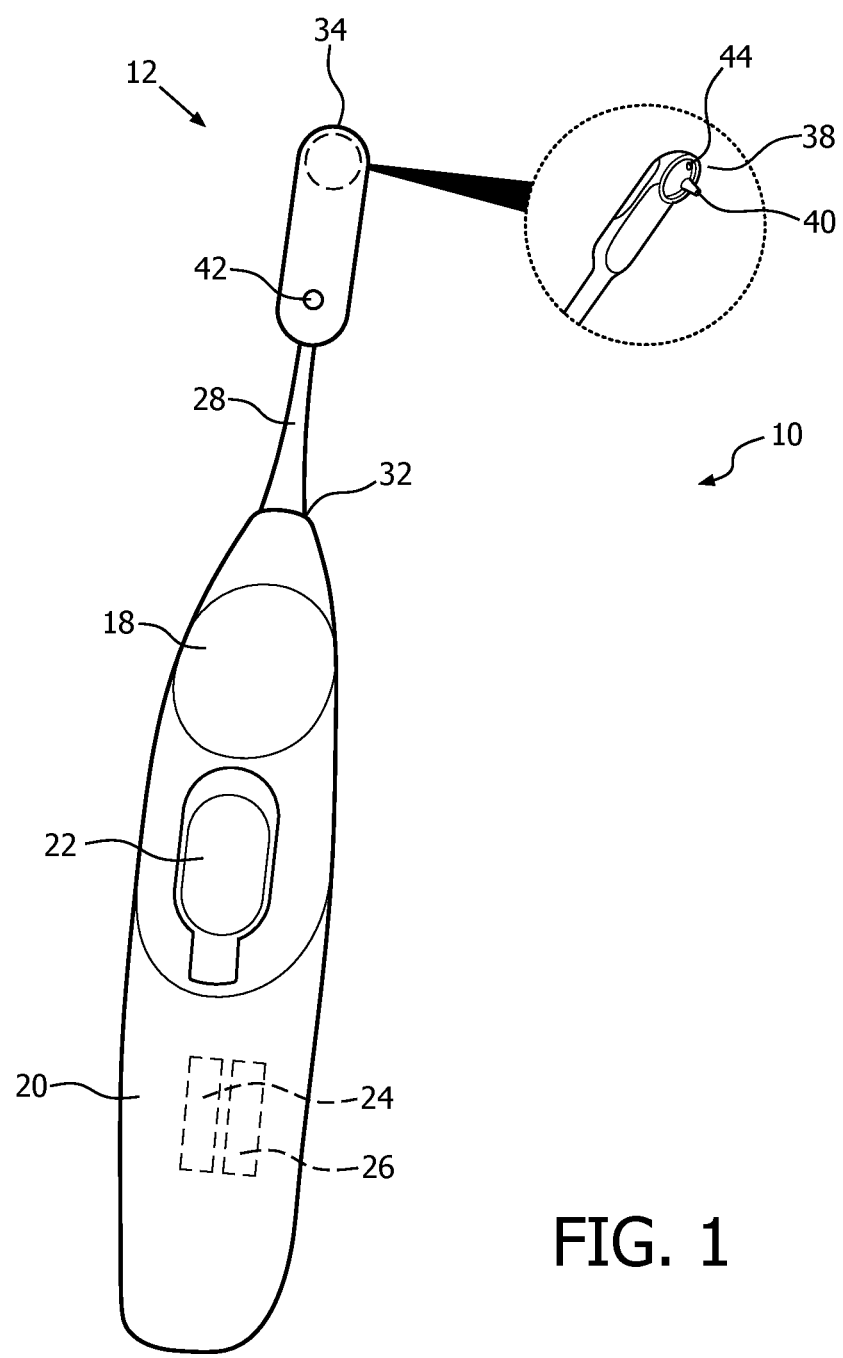
FIG. 1 is a perspective view of a device for powder delivery to interproximal areas of teeth and for implementing a dry powder delivery procedure according to various embodiments of the present disclosure.

With reference now to FIG. 1, there is shown a perspective view of a device 10 for powder delivery to interproximal areas of teeth and for implementing a powder delivery procedure according to various embodiments of the present disclosure. The device 10 includes a user replaceable powder delivery nozzle 12 according to an embodiment of the present disclosure. The device further includes an activation button 18, handle 20, liquid reservoir 22, control electronics 24, and at least one microburst pump 26. The user replaceable powder delivery nozzle 12 generally includes an elongated body 28 with at least one channel (30, FIG. 2) extending from a proximal end 32 of the nozzle to a distal end 34 of the nozzle, and a guidance tip 38 with at least one orifice 40 coupled to the at least one channel.

Nozzle 12 further comprises an air intake port 42 and a powder outlet port 44, as will be discussed further herein with reference to FIG. 2. Responsive to coupling of the proximal end 32 of the elongated body of the nozzle 12 to a distal end of the handle 20, an appropriate fluidic connection is established between the at least one reservoir 22 in the device and the at least one orifice 40, via the at least one channel (30, FIG. 2).

Figure 2:
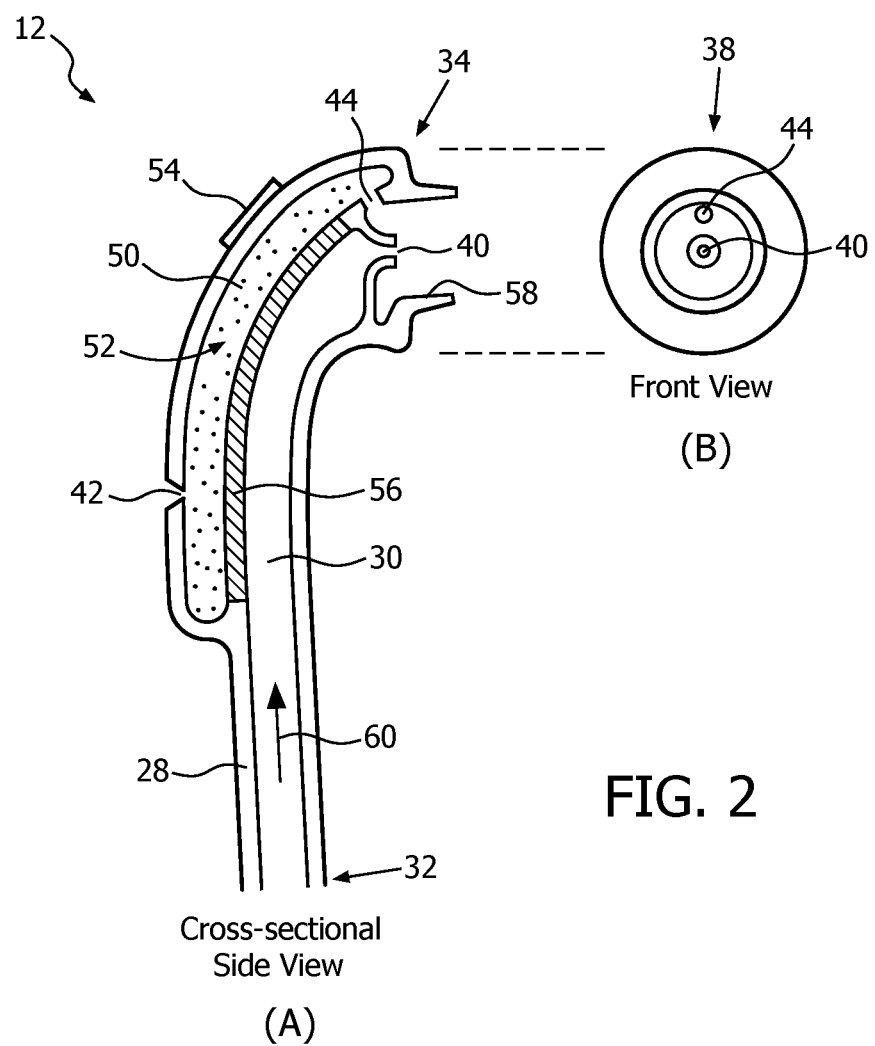
FIG. 2 is a schematic cross-sectional view of various components of a powder delivery nozzle for use with the device for powder delivery to interproximal areas of teeth and for implementing a powder delivery procedure according to an embodiment of the present disclosure.

Turning now to FIG. 2, there is shown a schematic cross-sectional view (FIG. 2A) of various components of a powder delivery nozzle 12 for use with the device 10 for powder delivery to interproximal areas of teeth and for implementing a powder delivery procedure according to an embodiment of the present disclosure. FIG. 2B illustrates a front view of the guidance tip 38.

As indicated above, the powder delivery nozzle 12 for a personal care appliance comprises a body 28 having at least one air-liquid channel 30 configured for delivery of air and/or liquid from a proximal end 32 to a distal end 34 thereof. The guidance tip 38 is located at the distal end 34 of the body and includes an orifice 40 coupled to the air-liquid channel 30. The orifice 40 is configured to expel a pulse of air and/or liquid.

The nozzle 12 also includes a powder chamber 50 located proximate the distal end 34 of the nozzle 12 for storing a powder 52 and having at least one air intake port 42 and at least one powder outlet port 44. In one embodiment, the powder chamber 50 further comprises a refillable chamber having a refill aperture and cap 54 wherein the refill aperture and cap 54 are configured (i) for being opened to enable refilling of the refillable chamber with powder and (ii) for being closed subsequent to refilling the refillable chamber with a desired powder. The refill aperture includes the refill cap, wherein removal of the refill cap enables the refilling via the refill aperture and replacement of the refill cap facilitates closing of the refill aperture.

With reference still to FIG. 2, nozzle 12 further includes a flexible membrane 56 disposed between a portion of the powder chamber 50 and the air-liquid channel 30. In one embodiment, flexible membrane 56 comprises any suitable flexible material. Typical suitable flexible membrane materials are rubbers, such as for example silicone rubber. An advantage of rubbers is that they are highly elastic. After an air pressure pulse application, a rubber membrane will relax to its original shape and give the powder chamber the original volume by ambient air filling the gap that was created therein by the released powder. It will be understood in the art that by choosing the right Shore A hardness, and making the rubber membrane the right thickness and size for a given nozzle implementation, a working membrane can be designed that will be soft enough that it can be moved by the air pressure pulse, but also strong enough that it will return to its original shape, pulling in the ambient air through the air intake port 42. In addition, if this will be used to deliver contents into the human mouth, the suitable flexible material will comprise one approved for containing oral ingestible materials.

In one embodiment, the at least one air intake port 42 comprises a one-way air intake valve and the at least one powder outlet port 44 comprises a one-way ejection valve. In addition, the air intake port 42 and the powder outlet port 44 are oriented or disposed in opposite directions, the intake port 42 further being proximate one end of powder chamber 50 and the powder outlet port 44 being proximate the other end of powder chamber. In addition, the air intake port 42 should be located far enough from the guidance tip 38 that the air intake port 42 is always outside of the mouth during use, i.e., to prevent any contaminants (e.g. saliva) from getting into the powder chamber. In one embodiment, the air intake port could be located closer to the proximal end or base of the nozzle. For example, the powder chamber may extend close to the base of the nozzle, and/or a suitable channel or tubing could be integrated within the nozzle that extends between the air intake port 42 at the base of the powder chamber to a position near the base of the nozzle. Furthermore, the powder outlet port 44 is disposed within the guidance tip 38, proximate the orifice 40. Moreover, the powder outlet port 44 is positioned within the guidance tip 38 at a depth that comprises one selected from the group consisting of (i) at a same depth as that of the orifice 40 and (ii) at a depth greater than a depth of the orifice 40 within the guidance tip 38.

As illustrated in FIG. 2, the powder outlet port 44 is positioned within the guidance tip 38 at a depth greater than a depth of the orifice 40 within the guidance tip 38. Preferably, the powder outlet port 44 is positioned within the guidance tip 38 such that fluid expelled via orifice 40 does not interfere with or cause any undesirable blockage of the powder outlet port 44. It should be noted that the embodiment of FIG. 2B in which the orifice 40 is centered within the guidance tip and the powder outlet port 44 is off-center is not limiting, as other spatial configurations of the powder outlet port 44 with respect to the orifice 40 are possible.

In another embodiment, the guidance tip 38 includes a distance piece 58 in the form of a suitable spacer for use in establishing, during use of the device 10 with nozzle 12, a desired spacing between the orifice 40 and the user's teeth, and between the powder outlet port 44 and the user's teeth. For example, the distance piece 58 can comprise a shape in the form of a ring, or other suitable shape, extending from the distal end of the nozzle 12 at the guidance tip 38. The distance piece can further comprise an integral portion of the nozzle or could also comprise a removable distance piece, the latter being selectable among a plurality of distance pieces of different distance dimensions, allowing a user to select a distance best suited for the individual user. The removable distance piece can be coupled to the guidance tip 38 using any suitable method, such as a press fit, threaded connection, or similar method.

In one embodiment, such as illustrated in FIG. 2, the powder chamber 50 is integrated in the nozzle 12, with the powder exit (i.e., powder outlet port 44) at or close to the fluid exit (i.e., orifice 40) of the nozzle. The chamber wall connected to the inside of the cleaning fluid channel (i.e., air-liquid channel 30) is made of flexible material (i.e., flexible membrane 56). When an air (or air-liquid) pressure pulse moves through the nozzle, the elevated pressure compresses the powder chamber, via the flexible material, releasing a dose of powder from the powder exit which ejects the powder in the air (or air-liquid) stream outside the orifice, transporting it to the teeth. In another embodiment, the powder may be delivered immediately to the teeth by the ejection speed out of the powder exit, without entering the air/liquid stream.

Stated another way, in operation, responsive to delivery of a pulse of air, liquid, or a combination of air and liquid via the air-liquid channel 30, in a direction 60 of an air-liquid pulse provided via fluid system within handle 20, a pulse of pressure is applied to the flexible membrane 56 for actuating a release of powder 52 expelled from the powder chamber 50 via the powder outlet port 44. In one embodiment, the release of powder comprises a desired dose of powder for a given application of dry powder. The air intake port 42 is configured for enabling air or an ambient gas to enter the powder chamber 50 immediately subsequent to the release of powder expelled via the outlet port 44 in proportion to the dose of powder expelled. For instance, immediately subsequent to the release of powder, air or an ambient gas enters the powder chamber 50 via the air intake port 42 in proportion to an amount of powder expelled, in preparation for a subsequent delivery of powder.

Responsive to activating at least one operational mode, via activation button 18, while directing the guidance tip 38 towards an interproximal area between teeth, the at least one microburst pump 26 is operable, via control electronics 24, (i) at a first setting to pump the liquid from the reservoir 22 via the first channel 30 to the at least one orifice 40. Further responsive to activating the at least one operational mode while directing the guidance tip 38 towards an interproximal area between teeth, the at least one microburst pump 26 is operable (ii) at a second setting, which could be the same or different from the first setting, to pump the dry powder from the powder chamber 50 via the powder outlet port 44 proximate the at least one orifice 40. The powder outlet port 44 expels the dry powder for delivering and depositing expelled dry powder onto the surfaces of teeth in and/or around the interproximal area.

Stated in a different manner, FIG. 2 illustrates a nozzle design with the flexible membrane 56 separating the air-liquid channel 30 from the powder chamber 50. As soon as an air (or air-liquid) pulse comes in contact with the flexible membrane 56, the flexible membrane will push a certain volume of powder 52 from the powder chamber 50 out of the powder chamber exit 44 (i.e., powder outlet port). The exit 44 can comprise, for example, a flexible duckbill valve, to prevent fluid from entering the dry powder chamber 50. The cleaning air-liquid nozzle exit 40 (i.e., cleaning orifice) is held at the optimal distance from the teeth with a cylindrical distance piece or cone 58. To allow the powder 52 to enter the air (or air-liquid) stream, the powder exit 44 is either positioned inside the distance piece 58, as shown in FIG. 2, or is positioned outside the distance cone, but ejecting the powder through a hole (or suitable aperture) in the cone, thereby reaching the air (or air-liquid) stream. In another embodiment, the powder is directed to a tooth/gum portion outside of the cone, and could even be directed to a previously cleaned interproximal space, wherein the powder exit is positioned one tooth beyond the cleaning orifice, with the nozzle being kept parallel to the teeth arch and cleaning started in the back of the mouth working forward. After the air (or air-liquid) shot or pulse, the powder chamber 50 will return back to its original volume, and air can enter the chamber through another duckbill valve 42 (i.e., the air intake port).

As also shown in FIG. 2, the channel towards valve 42 is illustrated relatively high on the nozzle, i.e., proximate the distal end 34. It should be noted that the location for air entry into valve 42 from the outside, subsequent to ejecting powder out exit 44, should remain outside the mouth. Accordingly, the channel towards valve 42 may be elongated downward, to create an air entrance closer to the handle 20, keeping the valve 42 outside the mouth when in use. The air inside the powder chamber 50 helps to transport the powder 52 through exit valve 44, especially at a later stage in the process, when the powder chamber contains less powder and contains more air. This will also help to keep the dose of powder delivered at a constant level, as in the beginning the dose amount can be high due to the complete filling with powder, and at the end it can be high due to the stronger air flow coming out of the powder chamber, transporting the powder more effectively. To refill the powder chamber 50, the cap 54 can be opened.

Figure 3:
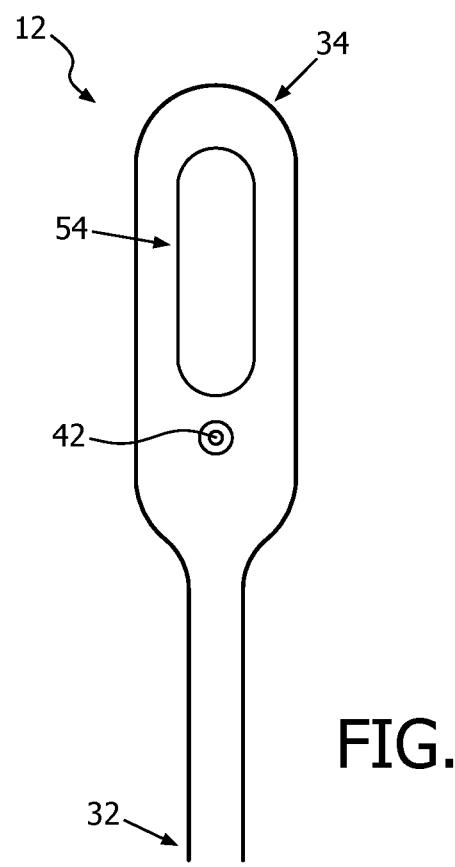
FIG. 3 is a perspective view of a powder delivery nozzle for use with the device for powder delivery to interproximal areas of teeth and for implementing a powder delivery procedure according to an embodiment of the present disclosure.

With reference now to FIG. 3, there is shown a perspective view of a powder delivery nozzle 12 (i.e., viewed from a back outside surface of the nozzle) for use with the device 10 for dry powder delivery to interproximal areas of teeth and for implementing a dry powder delivery procedure according to an embodiment of the present disclosure. As illustrated, the air intake port 42 is disposed on a back surface of the nozzle, near one end of the powder chamber closest to the proximal end 32 of the nozzle.

With reference now to FIG. 4, there is shown another perspective view of a powder delivery nozzle 12 (i.e., viewed from one side, more towards a front outside surface of the nozzle) for use with the device 10 for powder delivery to interproximal areas of teeth and for implementing a powder delivery procedure according to an embodiment of the present disclosure. As illustrated, the powder outlet port 44 is disposed on a front surface of the nozzle, near an opposite end of the powder chamber closest to the distal end 34 of the nozzle. In this illustration, the powder outlet 44 is shown located within the guidance tip 38, proximate the cleaning orifice 40. In addition, the cleaning orifice 40 is shown extending beyond the distance piece 58.

Turning now to FIG. 5, there is shown a schematic cross-sectional view of various components of a powder delivery nozzle 12 for use with the device 10 for powder delivery to interproximal areas of teeth and for implementing a powder delivery procedure according to another embodiment of the present disclosure. The embodiment of FIG. 5 is similar to that shown in FIG. 2, with the following differences. As illustrated in FIG. 5, the powder chamber 50 comprises an exchangeable powder chamber cartridge 62, wherein the flexible membrane 56 comprises a portion of the powder chamber 50 of the exchangeable cartridge (or the membrane can be on the nozzle). The exchangeable cartridge 62 is preferably without a removable refill cap, although a removable refill cap could be provided if needed or desired. The exchangeable cartridge 62 is further configured for attachment to the body 28, using any suitable attachment method. When attached, a suitable seal is formed between the flexible membrane 56 and the air-liquid channel 30, such that delivery of the powder is accomplished in a manner as discussed herein above. The exchangeable cartridge 62 can comprise, for example, a "click-in place" type component or similar component.

The type of powder to be used is not a particular subject of the embodiments of the present disclosure, however, some details will be disclosed below to render an understanding of the embodiments of the present disclosure more tangible. To prevent the powder from being inhaled, particles should typically be larger than 10 micrometer in diameter. A typical powder size to be used may be around 0.1 mm diameter particles. The amount of powder needed to coat all interproximal spaces (ca 5000 $mm^2$) in a user's mouth with a layer of 0.1 mm powder would be approximately 0.5 ml, which can easily be contained in a small chamber attached to the nozzle. The particles may contain a polymer and the active oral agent to be released. An example polymer could be poly (methyl vinyl ether/maleic acid) copolymer (Gantrez™), which is known to adhere well to the teeth, and can hold and slowly release active oral care agents. When such a dry polymer particle hits a wet surface it will immediately adhere, start swelling and will attach even more firmly. Active oral care agents can be antimicrobial agents, fluorides (anti-caries) or more specific beneficial agents (e.g. anti-sensitivity). Powder formulations for delivery of therapeutics are very common in medicine, e.g. inhalation drugs, but also powders are extensively used in the food industry. Manufacturing of such powders is commonly known in the art, and thus does not need further explanation here.

According to another embodiment, a method for delivering powder via a nozzle of a personal care appliance comprises providing a body having at least one air-liquid channel configured for delivery of air, liquid, or a combination of air and liquid from a proximal end to a distal end thereof. The method also comprises providing a guidance tip located at the distal end of the body, wherein the guidance tip includes an orifice coupled to the air-liquid channel and is configured to expel a pulse of air, liquid, or a combination of air and liquid. The method further comprises storing a powder within a powder chamber, the powder chamber having at least one air intake port and at least one powder outlet port; and disposing a flexible membrane between a portion of the powder chamber and the air-liquid channel, wherein responsive to delivery of a pulse of air, liquid, or a combination of air and liquid via the air-liquid channel, a pulse of pressure is applied to the flexible membrane for actuating a release of powder expelled from the powder chamber via the powder outlet port. Advantageously, the powder can be released outside the nozzle in the stream of air/liquid as it is being expelled from the nozzle.

In one embodiment of the method, the air intake port is configured for enabling air or an ambient gas to enter the powder chamber immediately subsequent to the release of powder expelled via the outlet port in proportion to a dose of powder expelled. In another embodiment, immediately subsequent to the release of powder, air or an ambient gas enters the powder chamber via the air intake port in proportion to an amount of powder expelled, in preparation for a subsequent delivery of powder.

According to yet another embodiment, a personal care appliance for delivery of dry powder to interproximal areas of teeth comprises a dry powder delivery nozzle as disclosed herein. The personal care appliance further comprises at least one microburst pump configured for being coupled to the air-liquid channel, and a reservoir for holding at least one of a liquid and air for delivery, wherein the at least one microburst pump couples between the reservoir and the air-liquid channel. The appliance further comprises a controller for activating the at least one microburst pump in at least one operational mode. Responsive to activating the at least one operational mode while directing the guidance tip towards an interproximal area between teeth, the at least one microburst pump is operable to pump the at least one of the liquid and air from the reservoir via the air-liquid channel to the orifice and expel the at least one of the liquid and air therefrom onto the surfaces of teeth in the interproximal area. In addition, in one operational mode, responsive to delivery of a pulse of air, liquid, or a combination of air and liquid via the air-liquid channel, a pulse of pressure is applied to the flexible membrane for actuating a release of powder expelled from the powder chamber via the powder outlet port. In a further embodiment, the at least one operational mode can include (i) a lower pressure cleaning shot or pulse of liquid and air, the lower pressure cleaning shot being insufficient to actuate a release of powder, and (ii) a higher pressure shot or pulse of air only, the higher pressure being sufficient to actuate the release of powder.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in oral care products and other applications where powder delivery is needed in confined spaces. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. A powder delivery nozzle for a personal care appliance, the nozzle comprising:
a body having at least one air-liquid channel configured for delivery of air, liquid, or a combination of air and liquid from a proximal end to a distal end thereof;
a guidance tip located at the distal end of the body, wherein said guidance tip includes an orifice coupled to the air-liquid channel and configured to expel a pulse of air, liquid, or a combination of air and liquid;
a powder chamber for storing a powder and having at least one air intake port and at least one powder outlet port disposed within the guidance tip; and
the nozzle having a flexible membrane disposed between a portion of the powder chamber and the air-liquid channel and configured to compress the powder chamber to expel powder via the powder outlet port, wherein responsive to delivery of a pulse of air, liquid, or a combination of air and liquid via the air-liquid channel, a pulse of pressure is applied to the flexible membrane to compress the powder chamber and actuate a release of powder expelled from the powder chamber via the powder outlet port.

2. The nozzle of the claim 1, wherein the air intake port comprises a one-way air intake valve for enabling air or an ambient gas to enter the powder chamber upon the release of powder expelled via the outlet.

3. The nozzle of claim 1, wherein the at least one air intake port comprises a one-way air intake valve and wherein the at least one powder outlet port comprises a one-way ejection valve.

4. The nozzle of claim 1, wherein the powder outlet port is disposed proximate the orifice.

5. The nozzle of claim 1, wherein the powder outlet port is positioned at a depth greater than a depth of the orifice within the guidance tip to prevent powder blocking the powder outlet port.

6. The nozzle of claim 1, wherein the powder chamber further comprises at least one selected from the group consisting of (i) a chamber integrated within the body, and (ii) an exchangeable chamber configured for attachment to the body.

7. The nozzle of claim 1, wherein the powder chamber further comprises a refillable chamber having a refill aperture, wherein the refill aperture is configured (i) for being opened to enable refilling of the refillable chamber with powder and (ii) for being closed subsequent to refilling the refillable chamber with powder.

8. A method for delivering powder via a nozzle of a personal care appliance, comprising:
providing a body of the nozzle, the body having at least one air-liquid channel configured for delivery of air, liquid, or a combination of air and liquid from a proximal end to a distal end thereof;
providing a guidance tip of the nozzle, the guidance tip located at the distal end of the body, wherein said guidance tip includes an orifice coupled to the air-liquid channel and configured to expel a pulse of air, liquid, or a combination of air and liquid;
storing a powder within a powder chamber of the nozzle, the powder chamber having at least one air intake port and at least one powder outlet port disposed within the guidance tip; and
disposing a flexible membrane between a portion of the powder chamber and the air-liquid channel, wherein responsive to delivery of a pulse of air, liquid, or a combination of air and liquid via the air-liquid channel, a pulse of pressure is applied to the flexible membrane for actuating a release of powder expelled from the powder chamber via the powder outlet port.

9. The method of claim 8, wherein the air intake port is configured for enabling air or an ambient gas to enter the powder chamber immediately subsequent to the release of powder expelled via the outlet port in proportion to a dose of powder expelled.

10. The method of claim 8, wherein the at least one air intake port comprises a one-way air intake valve and wherein the at least one powder outlet port comprises a one-way ejection valve.

11. The method of claim 8, wherein the powder outlet port is proximate the orifice.

12. The method of claim 8, wherein the powder outlet port is positioned at a depth that comprises one selected from the group consisting of (i) at a same depth as that of the orifice and (ii) at a depth greater than a depth of the orifice within the guidance tip.

13. The method of claim 8, wherein the powder chamber comprises at least one selected from the group consisting of (i) a chamber integrated within the body, and (ii) an exchangeable chamber configured for attachment to the body.

14. The method of claim 8, wherein the powder chamber further comprises a refillable chamber having a refill aperture, wherein the refill aperture is configured (i) for being opened to enable refilling of the refillable chamber with powder and (ii) for being closed subsequent to refilling the refillable chamber with powder.

\* \* \* \* \*